(12) United States Patent
Boehm et al.

(10) Patent No.: US 6,707,881 B2
(45) Date of Patent: Mar. 16, 2004

(54) X-RAY DIAGNOSTIC INSTALLATION HAVING A PLANAR SOLID STATE X-RAY IMAGE CONVERTER

(75) Inventors: Stefan N. Boehm, Oberasbach (DE); Gerhard Hahm, Erlangen (DE); Martin Spahn, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/205,936

(22) Filed: Jul. 25, 2002

(65) Prior Publication Data
US 2003/0035509 A1 Feb. 20, 2003

(30) Foreign Application Priority Data
Jul. 25, 2001 (DE) .......................... 101 36 239

(51) Int. Cl.⁷ ................................ H05G 1/64
(52) U.S. Cl. ................ 378/98.7; 378/98.12; 378/207
(58) Field of Search .............. 378/98.7, 98.8, 378/98.12, 207

(56) References Cited

U.S. PATENT DOCUMENTS

| | | | |
|---|---|---|---|
| 4,174,525 A | * 11/1979 | Dechering et al. | 348/331 |
| 4,360,834 A | * 11/1982 | Schmale et al. | 348/331 |
| 5,452,338 A | * 9/1995 | Granfors et al. | 378/98.11 |
| 5,617,461 A | 4/1997 | Schreiner | 378/98.5 |
| 5,778,044 A | * 7/1998 | Bruijns | 378/98.7 |
| 6,130,932 A | * 10/2000 | Diepstraten | 378/98.7 |
| 6,219,405 B1 | * 4/2001 | Inoue | 378/98.8 |

FOREIGN PATENT DOCUMENTS

DE    199 15 851    7/2000

* cited by examiner

Primary Examiner—Edward J. Glick
Assistant Examiner—Allen C. Ho
(74) Attorney, Agent, or Firm—Schiff Hardin & Waite

(57) ABSTRACT

An X-ray diagnostic installation has an X-ray tube, a voltage generator, a planar solid state X-ray image converter for generating raw images, an image system and a playback device. The image system has a device for offset correction that acquires an offset image and stores it in a correction offset memory. The correction offset memory is preceded by a microphony detector that analyzes the current offset image for disturbances due to microphony and allows storage only of a current offset image, that is free of such disturbances.

6 Claims, 7 Drawing Sheets

X-RAY DIAGNOSTIC INSTALLATION HAVING A PLANAR SOLID STATE X-RAY IMAGE CONVERTER

BACKGROUND OF THE INVENTION

1. Field of the Invention

The present invention is directed to an X-ray diagnostic installation of the type having an X-ray tube, an X-ray generator, a planar solid state X-ray image converter for generating raw images, an image system and a playback device, wherein the image system includes a device for offset correction that acquires an offset image and stores it in a correction offset memory.

2. Description of the Prior Art

FIG. 1 shows an X-ray diagnostic installation of the above type, as disclosed in German PS 195 27 148, having an X-ray tube 2 supplied with high-voltage and filament voltage by an X-ray generator 1 that emits a conical X-ray beam 3 that penetrates a patient 4 and generates radiation images on a solid state detector 5 that is sensitive to X-rays. The output signal of the solid-state detector 5, the image data 6, is supplied to an image system 7. The image system 7 can include converters, image memories and processing circuits. The image system 7 is connected to a monitor 8 for the playback of the acquired X-ray images. Operating elements 9 are connected to the other components of the X-ray diagnostic installation via a system control and communication 10.

FIG. 2 shows a cross-section of the solid state detector 5 in perspective. The basic components of the solid state detector 5 are composed of a solid state pixel matrix, line drivers and amplifiers. The solid state pixel matrix has a layer with a scintillator 11 composed, for example, of cesium iodide (CsI) that supplies photons in the visible spectrum to a pixel matrix 12 of amorphous silicon when irradiated with the X-ray beam 3, the photons producing a visible X-ray image. As shown enlarged in FIG. 2, each of the pixels or picture elements of this pixel matrix 12 is composed of a photodiode 13 and a switch 14 that is connected to row lines 15 and column lines 16. The pixel matrix 12 is applied on a glass substrate 19.

All pixels of a line are addressed and read out simultaneously by the line drivers 17. The signals are processed in parallel in a number of amplifiers 18. In the simplest case, an image is progressively read out line-by-line.

Newer solid state detectors for X-ray imaging, such as the solid state X-ray image detector 5, are based on active readout matrices of, for example, amorphous silicon (a-Si). The image information is converted in an X-ray converter, for example the scintillator 11, is stored in the photodiodes 13 of the matrix as electrical charge, and is subsequently read out with a dedicated electronics via the active switches 14 and is analog-to-digitally converted. The readout and drive chips, the line drivers 17 and amplifiers 18 are connected to the row lines 15 and column lines 16 of the active pixel matrix 12 with, for example, flexible interconnects (not shown). Electronic noise effects, referred to as microphony effects, can occur due to concussions experienced by the X-ray image converter 5, these being transmitted into the image content due to mechanical oscillations or vibrations during an image acquisition.

Pre-processing steps that are usually undertaken, such as flat fielding, i.e. offset correction and gain correction, as well as fault correction, are shown on the basis of FIG. 3. Since solid state X-ray image converters based on a-Si-like all semiconductor detectors—exhibit temperature dependencies, current offset images are constantly acquired as background and are stored. This correction offset image stored in memory 20 is normally utilized for correction by means of subtraction in a subtraction stage 22 from the raw image 21 stored in a memory as an unprocessed X-ray image. The offset image is taken into consideration either at 100% or in the form of an averaging with earlier offset images. The result is corrected by multiplication in a multiplication stage 24 with a gain image stored in a memory 23, so that an imaged referred to as a flat-fielded X-ray image is obtained, which is present in a memory 25 for further image processing with further processing electronics 26.

When the currently stored correction offset image in memory 20 (or one of the recent offset images given averaging methods) is disturbed due to the microphony effects caused, for example, by a blow to the exposure stand, pulling out the detector drawer or sitting on the X-ray table, the disturbance is consequently calculated into the further-processing of the X-ray image—the corrected image exhibits disturbances, artifacts, due to the microphonic effect. These artifacts can be substantial and locally destroy the image content.

Since no such detectors were previously available in the marketplace, the current problem did not arise.

Alternative solutions such as reducing the noise contribution of the current offset image by averaging a number of offset images, or mechanical damping of the detection suspension do not fundamentally solve the problem but only diminish it. Although the first solution would reduce the effect in the individual image, the noise effect would persist over longer times. The disturbance thus would have to be calculated in a number of X-ray images.

German OS 199 15 851 discloses a method wherein an offset-corrected raw image is corrected with reference to artifacts on the basis of data acquired from the dark reference zone in all instances, these artifacts being established by a detector model.

SUMMARY OF THE INVENTION

An object of the present invention is to provide an X-ray diagnostic installation of the type initially described wherein the disturbing influence of the microphonic effect is eliminated.

This object is inventively achieved in an installation of the type described above wherein the correction offset memory is preceded by a microphony detector as an analysis module that analyzes the current offset image for microphony disturbances and effects storage only of a current offset image that is disturbance-free. As a result, the current offset image is analyzed for microphony disturbances before a further-processing is permitted. When microphony disturbances are present, the analyzed offset image is discarded and is not utilized for further-processing—the most recently accepted offset image is then still the current one. When it is free of disturbances, i.e. when no microphony effects are detected, a disturbance-free, current offset image is read into the correction offset memory and "authorized" as a new, current offset image for the correction.

In this way, the problem is solved with relatively little outlay, for example with the assistance of a software analysis, and without complicated and expensive design modifications or improvements in the hardware or mechanics of the detectors or system.

Inventively, the microphony detector can be an analysis device with filters and/or threshold circuits for checking the current offset image for microphony, for example with a high-pass filter and a low-pass filter.

The microphony detector can include a correction device for the current offset image.

Calculating capacity and calculating time can be saved when the microphony detector is fashioned such that it analyzes only a part of the current offset image, for example only in the region of interest (ROI).

It has proven advantageous when the microphony detector is fashioned such that the current offset image is supplied to an offset correction unit, a gain correction unit and/or a fault correction unit. This has the advantage that the resulting image again normally fluctuates around a nominal zero value and that the normal image processing pipeline can be employed.

DESCRIPTION OF THE PREFERRED EMBODIMENTS

Figure 1:
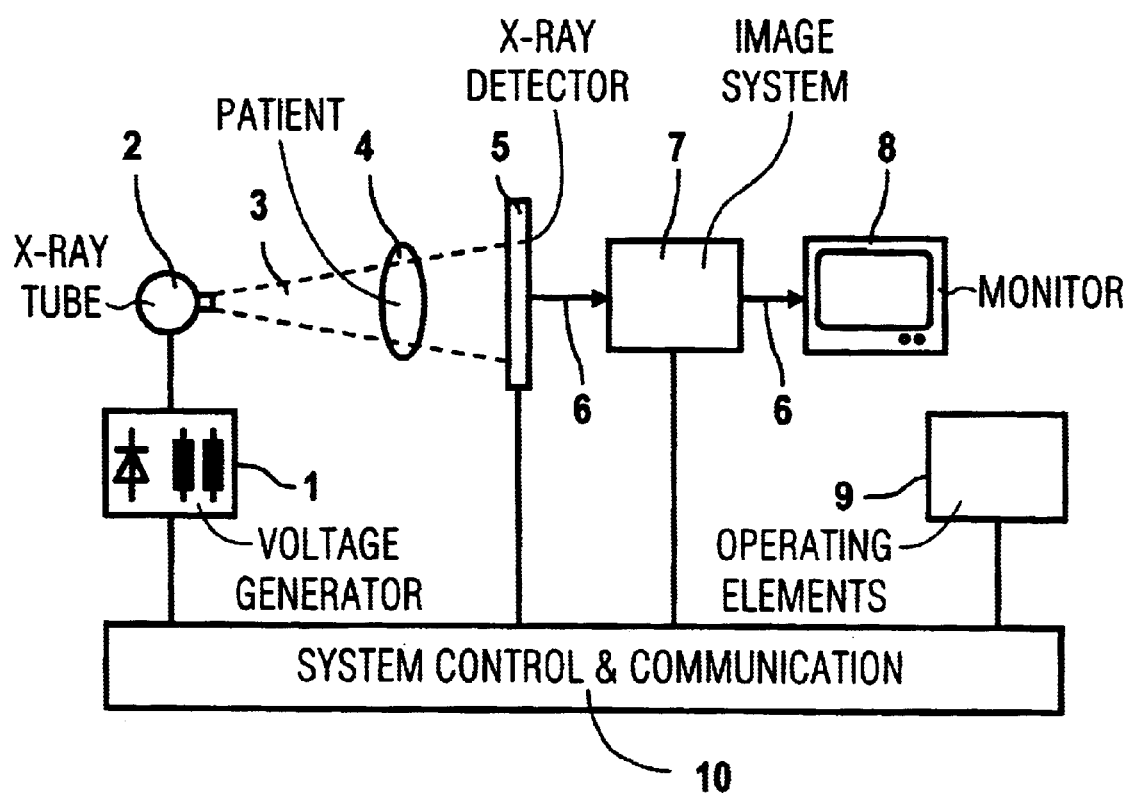
FIG. 1, as noted above, is a block diagram of a known X-ray diagnostic installation with a solid state X-ray image converter.
Figure 2:
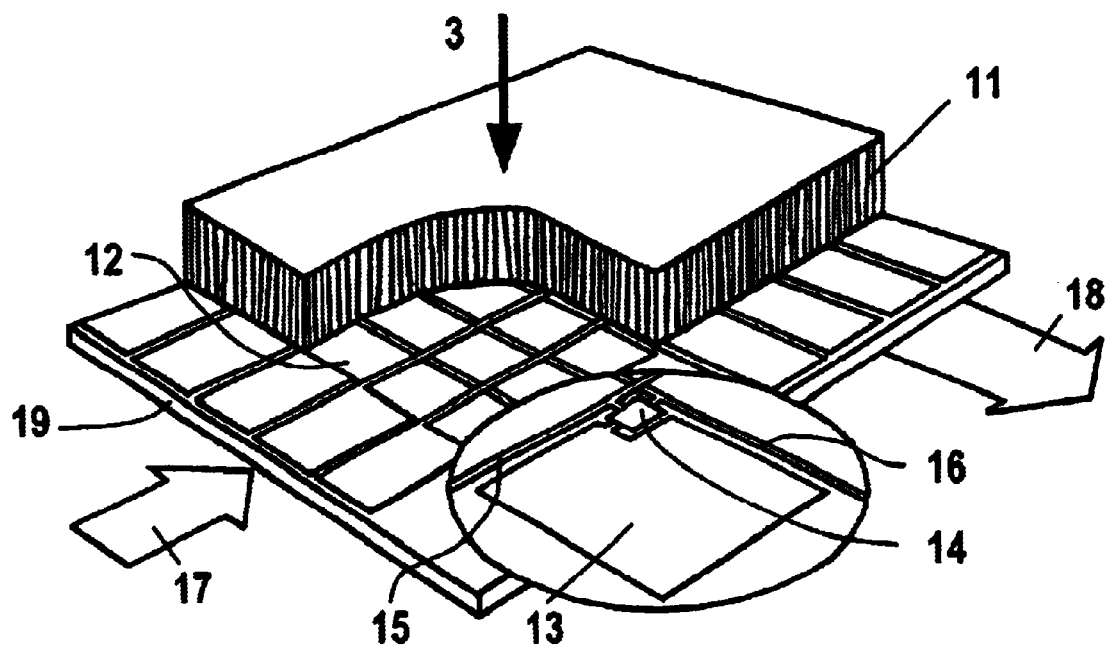
FIG. 2, as noted above, is a perspective view of a known X-ray image converter.
Figure 3:
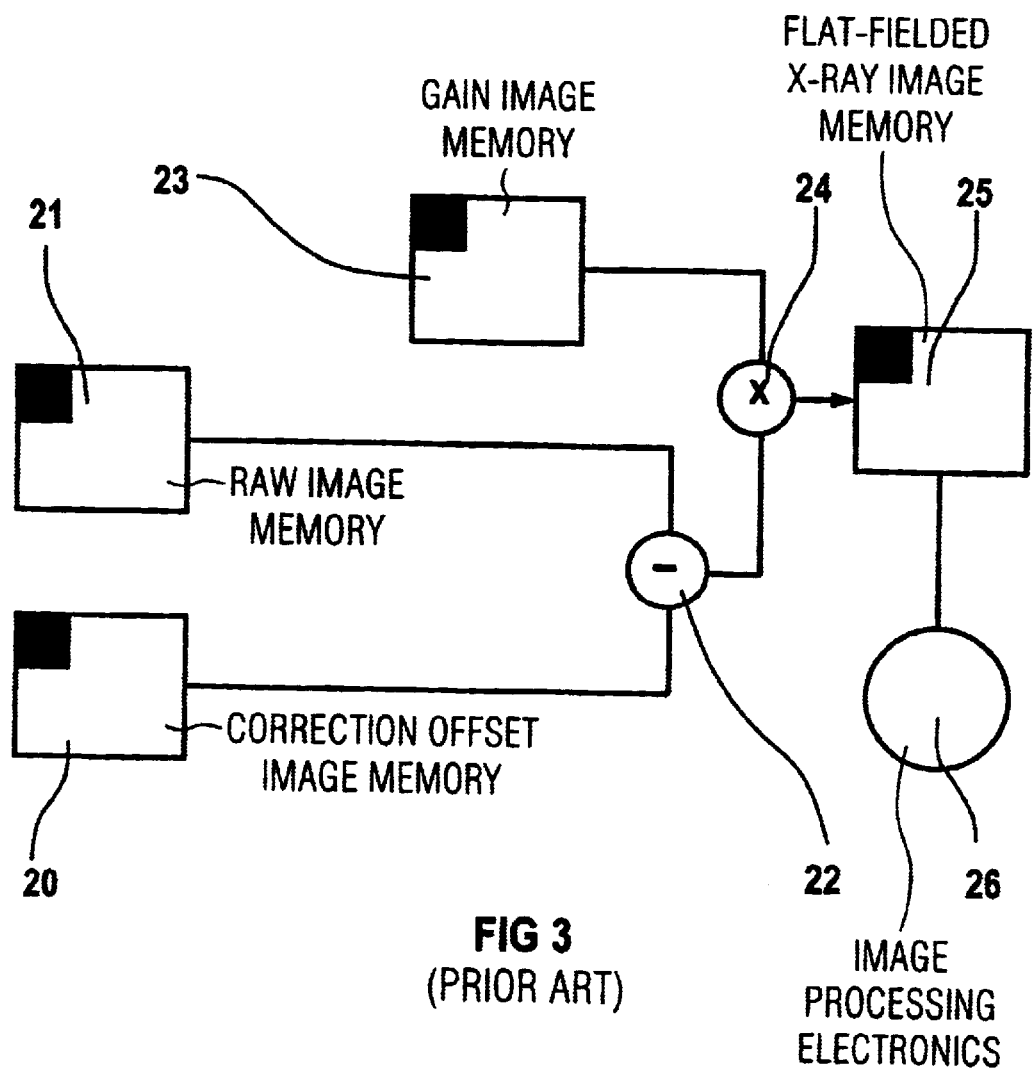
FIG. 3, as noted above shows components of the image system for the implementation of known pre-processing steps.
Figure 4:
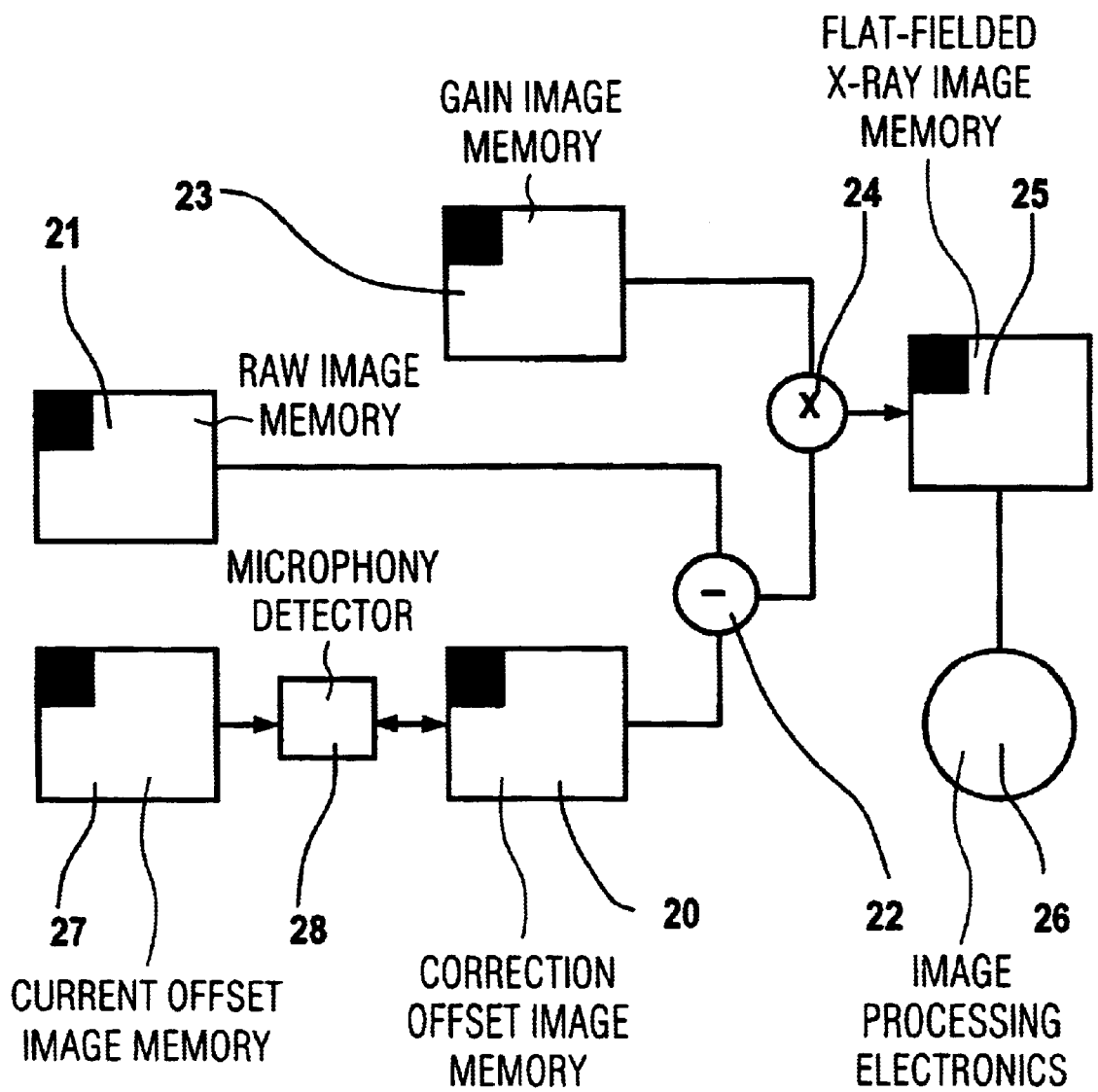
FIGS. 4–9 illustrates components of the image system for the implementation of the inventive pre-processing steps.
Figure 5:
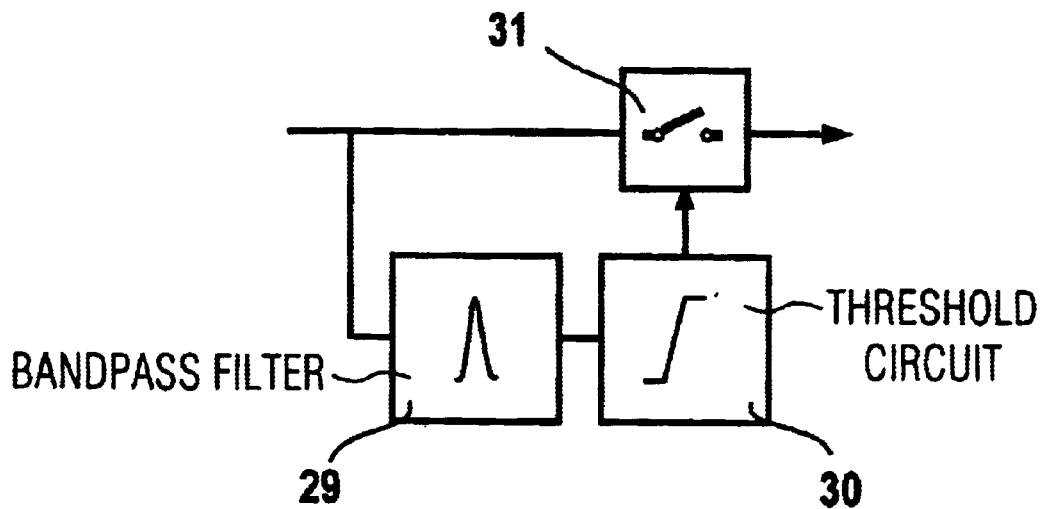

The inventive device is explained in greater detail in FIG. 4, wherein elements that are also present in FIG. 3 have the same reference numerals. Compared to the embodiment known from FIG. 3, the memory 20 for the stored correction image is preceded by a further memory 27 for a current offset image that is followed by a microphony detector 28 that recognizes disturbances produced by microphony and prevents a transfer of the current offset image into the memory 20 for the correction offset image if such disturbances are detected. Only noise-free offset images are stored.

When it is free of microphony effects, the correction offset image in the memory 20 can either be replaced by the current offset image in the memory 27 or a suitable averaging of the current offset images in the memory 27 is implemented.

FIGS. 5 through 9 show the microphony detector 28 in detail. In the simplest case according to FIG. 5, the microphony detector 28 has a filter, for example a band-pass filter 29, as well as a threshold circuit 30 with an upper and a lower threshold or limit value. The band-pass filter 29 is designed for the frequency of the noise signal due to the microphony. The threshold circuit 30 is provided so that even very slight concussions or other small noise signals do not cause the microphony detector 28 to preclude storage, the effect thereof being that only the offset image that lies within the limit values is allowed to pass and be stored.

The threshold circuit 30 has a switching stage 31 connected to it that suppresses a storage of the current offset image as the correction offset image when the thresholds are transgressed. When, in contrast, the output values of the threshold circuit 30 lie within the threshold range, i.e. no disturbances are present, then the current offset image from memory 27 is transferred into the memory 20 for the correction offset image.

In the exemplary embodiment according to FIG. 6, the current offset image in the memory 27 is corrected with the stored correction offset image in the memory 20 by subtraction and the resulting difference is subsequently analyzed by a threshold circuit 33. Disturbances that are greater than the expected pixel noise contributions are thereby recognized, and the current offset image in the memory 27 which produced this difference image is discarded.

Figure 6:
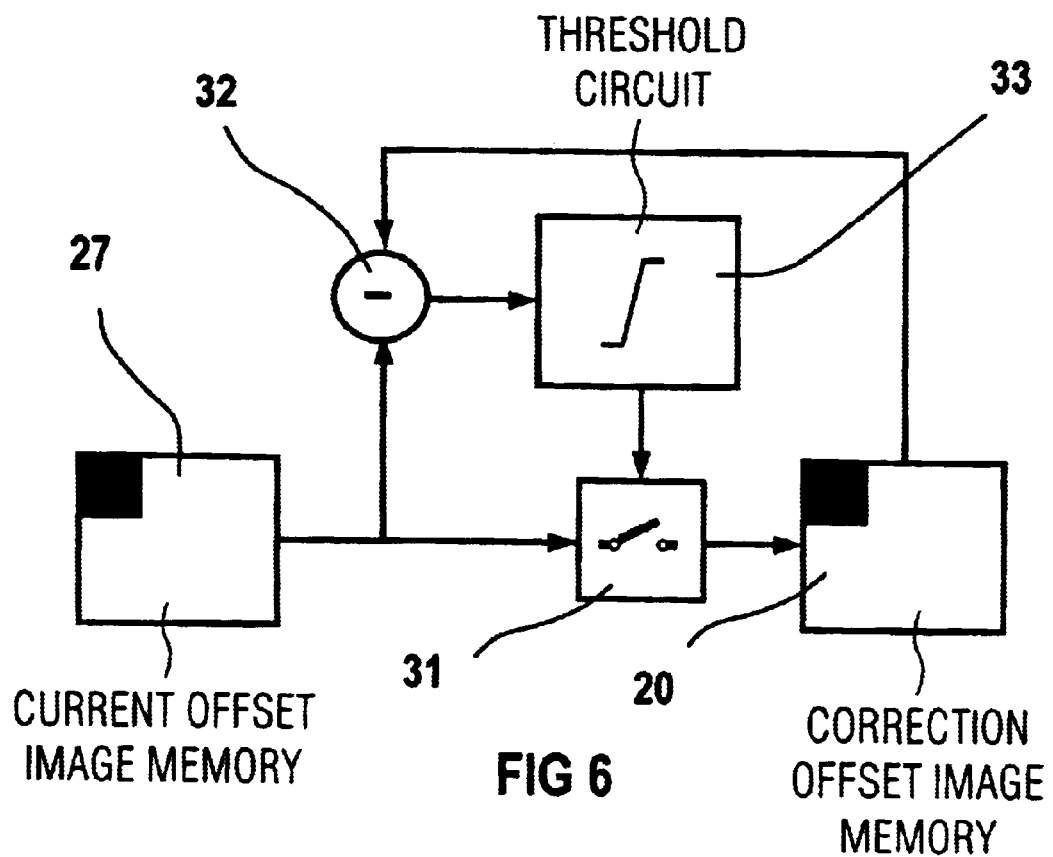
Figure 7:
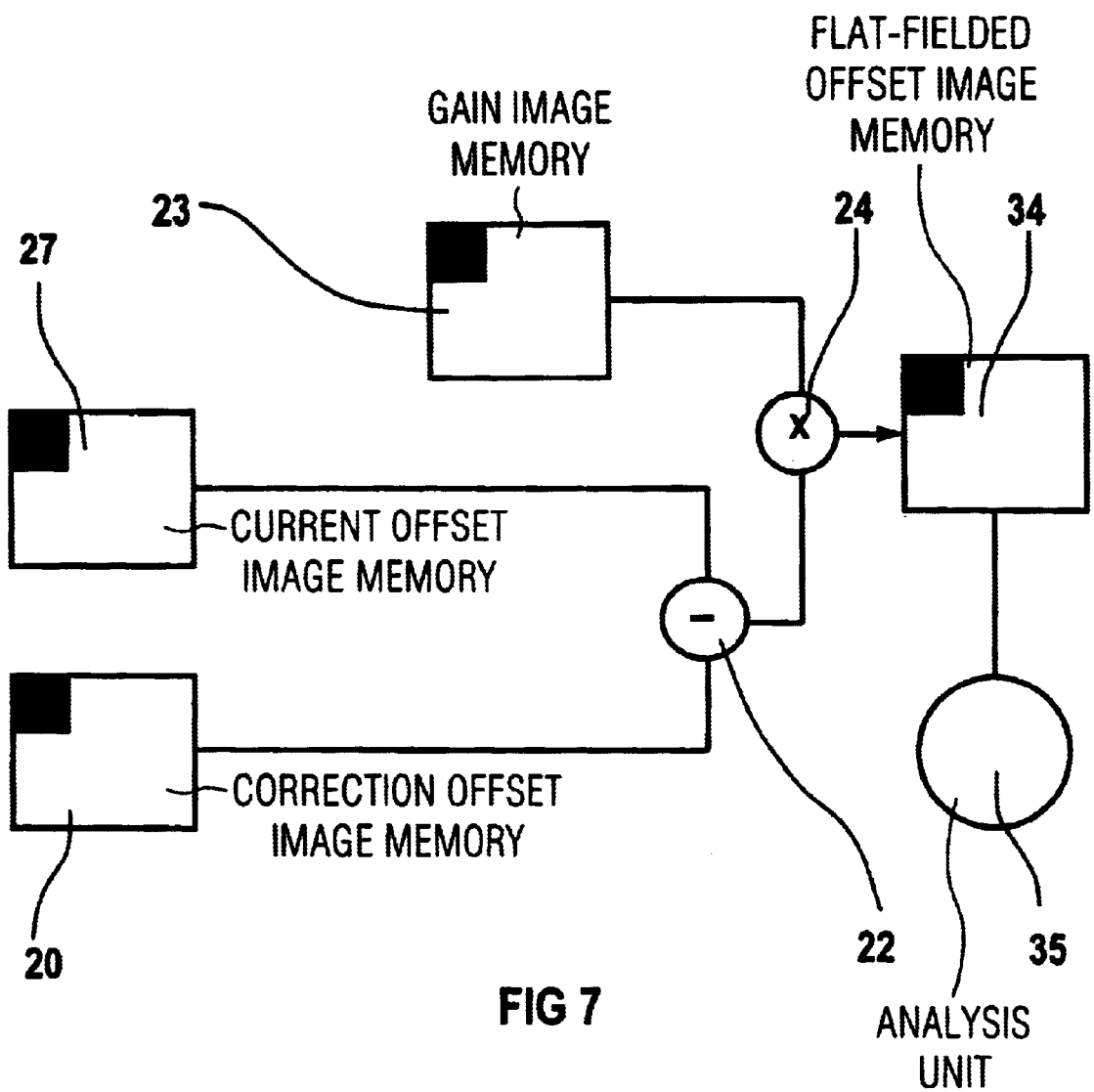

In the exemplary embodiment according to FIG. 7, the current offset image in the memory 27 is subjected to the same procedure as the raw image in the memory 21, i.e. the current offset in the memory image 27 is compared by subtraction in a subtraction stage 22 to the stored correction offset image in the memory 20, is corrected with the gain image in the memory 23 by multiplication in a multiplication stage 24, and is stored as a flat-fielded offset image in the memory 34. An analysis as described on the basis of FIG. 6 subsequently ensues in an analysis unit 35.

Figure 8:
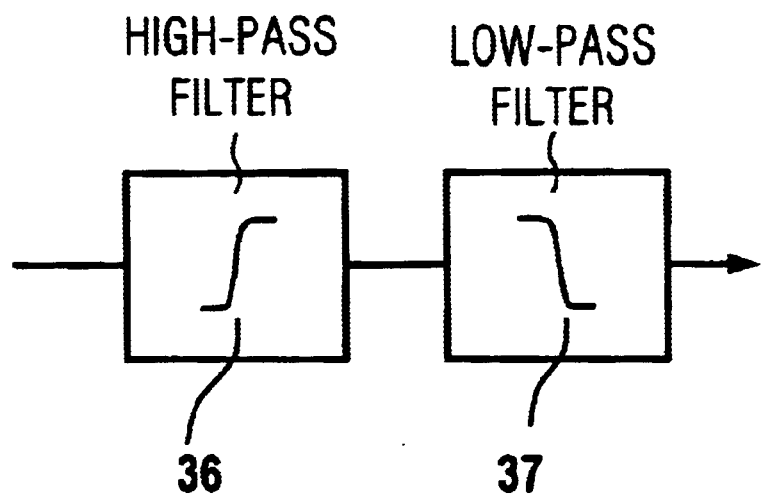

FIG. 8 describes another analysis that can replace the analysis according to FIG. 6 or FIG. 7. The current offset image from the memory 27 is first supplied to a high-pass filter 36 with a large filter kernel and the output signal thereof is supplied to a low-pass filter 37 with a small filter kernel. These filters 36 and 37 cause slight fluctuations around zero, for example due to temperature fluctuations or electrical offset fluctuations, to be eliminated and the pixel noise is suppressed. As a result, even very small microphony effects can be detected and suppressed.

Figure 9:
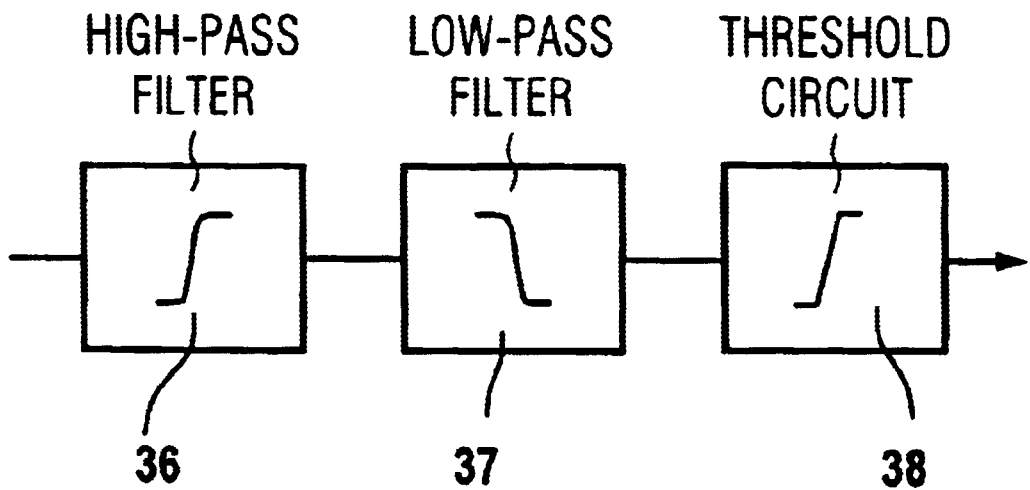

In the exemplary embodiment according to FIG. 9, the high-pass filter 36 and the low-pass filter 37 have a threshold circuit 38 added to them ensures that signals produced by faulty pixels cannot lead to a noise report (detection).

There are a number of possibilities for the implementation of the inventive X-ray diagnostic installation, a few of these being set forth summarized below as examples:

(i) The most recent offset image can be utilized for the analysis in its raw form and can be checked for microphony with suitable filters and limit values.

(ii) The most recent offset image is corrected with the most recent, current offset image, for example subtracted, and is subsequently analyzed. This has the advantage that the difference image normally fluctuates around zero and only exhibits the noise of the individual pixels. When the difference image exhibits disturbances that are greater than the anticipated pixel noise contributions, for example above an upper or below a lower threshold, the image is discarded.

(iii) The most recent offset image can be processed like a normal X-ray raw image, i.e. offset correction, gain correction and fault correction are carried out. This has the advantage that the resulting image again normally fluctuates around the zero and that the normal image processing pipeline can be employed. This is particularly helpful when hardware is employed therefor. The analysis ensues, for example, as in (ii).

(iv) The most recent offset image can be corrected as in (ii) or (iii). For the analysis, a high-pass with a large kernel is first formed and a low-pass with a small kernel is subsequently formed. These filters effect that slight fluctuations around zero, for example due to temperature fluctuations or electrical offset fluctuations, are eliminated and the pixel noise is suppressed. As a result, even very small microphony effects can be measured and eliminated.

(v) The most recent offset image can be processed as in (iv), but a minimum number of pixels must lie outside the upper and the lower thresholds. This avoids an individual faulty pixel or a few faulty pixels leading to the discarding of an offset image even though no microphony artifact is present.

(vi) Instead of being analyzed in its full resolution, the most recent offset image can be analyzed by underscanning on an image with, for example, different sampling frequencies in the x-direction and the y-direction or by sampling only in the region of interest (ROI). The time outlay for the analysis can thus be considerably reduced dependent on the sampling.

In the inventive fashioning of the X-ray diagnostic installation, the offset image is first investigated for disturbances and is only employed for further-processing when the offset image is noise-free. Normally, the offset image would be utilized for further-processing without having been checked. This could ensue without a problem if no disturbing microphony effects were to occur. However, a noise-free, current offset image from the memory 27 that updates the stored correction offset image in the memory 20 to be utilized for the correction still can always be generated by constant acquisition of offset images as background when the system requires no X-ray image.

Although modifications and changes may be suggested by those skilled in the art, it is the intention of the inventors to embody within the patent warranted hereon all changes and modifications as reasonably and properly come within the scope of their contribution to the art.

We claim as our invention:

1. An X-ray diagnostic installation comprising:

an X-ray tube which emits an X-ray beam;

an X-ray image converter on which said X-ray beam is incident, said X-ray image converter generating electrical signals representing a raw image subject to disturbances;

an image system supplied with said electrical signals for generating signals representing a visible image therefrom, said image system including a device for offset correction which generates an offset image from said electrical signals, a correction offset memory in which said offset image is stored, and an analysis module preceding said correction offset memory which analyzes said offset image to determine a presence of said disturbances therein and which allows storage of said offset image in said correction offset memory only if said offset image is free of said disturbances, and processing circuitry for generating said signals representing said visible image from said offset image; and a playback device to which said signals representing said visible image are supplied for playback of said visible image.

2. An X-ray diagnostic installation as claimed in claim 1 wherein said disturbances include microphony effects, and wherein said analysis module comprises a microphony detector containing at least one detector stage selected from the group consisting of a filter stage and a threshold circuit stage, for analyzing said offset image to determine whether said microphony effects are present in said offset image.

3. An X-ray diagnostic installation as claimed in claim 2 wherein said microphony detector includes said filter stage, and wherein said filter stage comprises a high-pass filter and a low-pass filter.

4. An X-ray diagnostic installation as claimed in claim 2 wherein said microphony detector includes a correction device for a current offset image.

5. An X-ray diagnostic installation as claimed in claim 2 wherein said microphony detector analyzes only a portion of said offset image.

6. An X-ray diagnostic installation as claimed in claim 1 further comprising a correction stage to which said offset image is supplied if said offset image is free of said disturbances, said correction stage being selected from the group consisting of an offset correction unit, a gain correction unit and a fault correction unit.

* * * * *